(12) United States Patent
Baccelli et al.

(10) Patent No.: US 7,637,950 B2
(45) Date of Patent: Dec. 29, 2009

(54) INTERVERTEBRAL IMPLANT WITH TOOTHED FACES

(75) Inventors: Christian Baccelli, Ayguemorte les Graves (FR); Jacques Senegas, Mérignac (FR); Evans Zeiger, Birmingham, AL (US); Tarcisio Barros, Sao Paolo (BR); Dietmar Salger, Retgendorf (DE); Franck Van Den Eeden, Massenar (NL)

(73) Assignee: Stryker Spine (FR)

( * ) Notice: Subject to any disclaimer, the term of this patent is extended or adjusted under 35 U.S.C. 154(b) by 0 days.

(21) Appl. No.: 10/124,153

(22) Filed: Apr. 17, 2002

(65) Prior Publication Data
US 2003/0028249 A1  Feb. 6, 2003

Related U.S. Application Data

(63) Continuation-in-part of application No. PCT/FR00/02899, filed on Oct. 18, 2000.

(30) Foreign Application Priority Data
Oct. 18, 1999  (FR)  .................................. 99 12951

(51) Int. Cl.
 *A61F 2/44* (2006.01)
(52) U.S. Cl. .................................. 623/17.11
(58) Field of Classification Search ............. 623/11.11, 623/16.11, 17.11–17.15, 17.16, 23–58; 606/60, 606/61
See application file for complete search history.

(56) References Cited

U.S. PATENT DOCUMENTS

| 5,192,327 | A |   | 3/1993  | Brantigan |            |
|-----------|---|---|---------|-----------|------------|
| 5,306,308 | A | * | 4/1994  | Gross et al. | 623/17.16 |
| 5,514,180 | A |   | 5/1996  | Heggeness et al. |       |
| 5,683,464 | A | * | 11/1997 | Wagner et al. | 623/17.16 |
| 5,713,899 | A | * | 2/1998  | Marnay et al. | 606/61 |
| 5,800,547 | A | * | 9/1998  | Schafer et al. | 623/17.16 |
| 5,865,845 | A |   | 2/1999  | Thalgott |            |
| 5,876,457 | A | * | 3/1999  | Picha et al. | 623/17.11 |
| 5,885,299 | A | * | 3/1999  | Winslow et al. | 606/99 |
| 5,888,227 | A | * | 3/1999  | Cottle | 623/17.16 |
| 5,968,098 | A | * | 10/1999 | Winslow | 623/17.11 |
| 5,989,289 | A | * | 11/1999 | Coates et al. | 623/17.16 |
| 6,019,793 | A | * | 2/2000  | Perren et al. | 623/17.16 |
| 6,025,538 | A | * | 2/2000  | Yaccarino, III | 128/898 |
| 6,210,412 | B1| * | 4/2001  | Michelson | 606/61 |

(Continued)

FOREIGN PATENT DOCUMENTS

CA          2338881          2/2000

(Continued)

OTHER PUBLICATIONS

Office Action from corresponding Japanese Application 2001-531060, dated Mar. 3, 2009.

*Primary Examiner*—Anu Ramana
(74) *Attorney, Agent, or Firm*—Lerner, David, Littenberg, Krumholz & Mentlik, LLP

(57) ABSTRACT

An intervertebral implant having two mutually opposite main faces and a side face, wherein at least one of the faces has mutually parallel shaped teeth. The general shape of the profile of the toothed face in at least one plane extending transversely to the face, is curved. Additionally, at least one spike projects from one of the main faces.

23 Claims, 4 Drawing Sheets

U.S. PATENT DOCUMENTS

| | | | |
|---|---|---|---|
| 6,241,771 B1 * | 6/2001 | Gresser et al. | 623/17.16 |
| 6,245,108 B1 * | 6/2001 | Biscup | 623/17.11 |
| 6,258,125 B1 * | 7/2001 | Paul et al. | 623/17.11 |
| 6,325,827 B1 * | 12/2001 | Lin | 623/17.16 |
| 6,454,805 B1 * | 9/2002 | Baccelli et al. | 623/17.11 |
| 6,482,233 B1 * | 11/2002 | Aebi et al. | 623/17.11 |
| 6,503,279 B1 * | 1/2003 | Webb et al. | 623/17.16 |
| 6,511,509 B1 * | 1/2003 | Ford et al. | 623/23.5 |
| 6,527,803 B1 * | 3/2003 | Crozet et al. | 623/17.11 |
| 6,547,823 B2 * | 4/2003 | Scarborough et al. | 623/17.16 |
| 6,558,423 B1 * | 5/2003 | Michelson | 623/17.11 |
| 6,629,998 B1 * | 10/2003 | Lin | 623/17.11 |
| 6,635,086 B2 * | 10/2003 | Lin | 623/17.11 |
| 6,805,714 B2 * | 10/2004 | Sutcliffe | 623/17.11 |
| 6,855,168 B2 * | 2/2005 | Crozet | 623/17.11 |
| 2002/0010511 A1 * | 1/2002 | Michelson | 623/17.15 |
| 2002/0177898 A1 * | 11/2002 | Crozet | 623/17.11 |
| 2003/0114854 A1 * | 6/2003 | Pavlov et al. | 606/61 |

FOREIGN PATENT DOCUMENTS

| | | |
|---|---|---|
| FR | 2 726 759 A1 | 5/1996 |
| FR | 2 727 003 | 5/1996 |
| FR | 2 782 914 A1 | 3/2000 |
| WO | 9909914 | 3/1999 |
| WO | 99/38461 A1 | 8/1999 |
| WO | WO 9966867 * | 12/1999 |
| WO | WO-00/13618 | 3/2000 |
| WO | WO-00/44320 | 8/2000 |
| WO | WO-01/03615 | 1/2001 |
| WO | WO-01/15637 | 3/2001 |

* cited by examiner

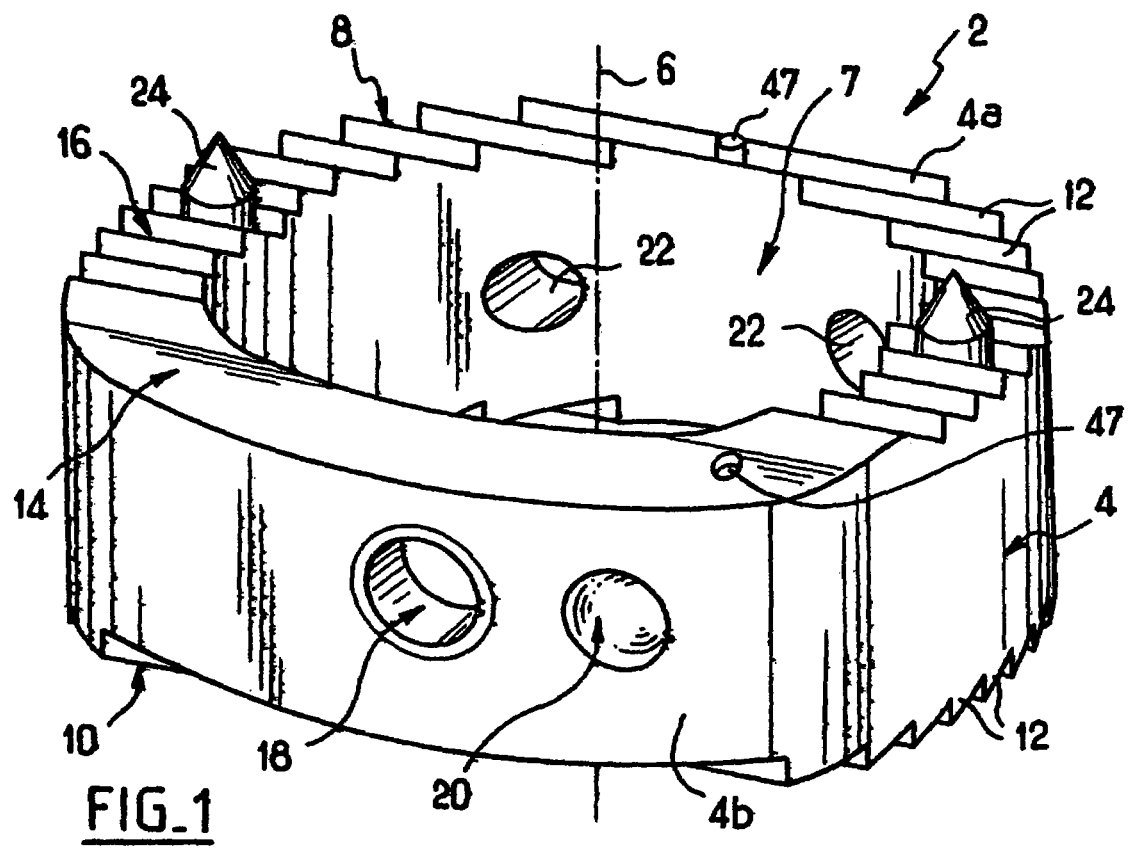
FIG_1
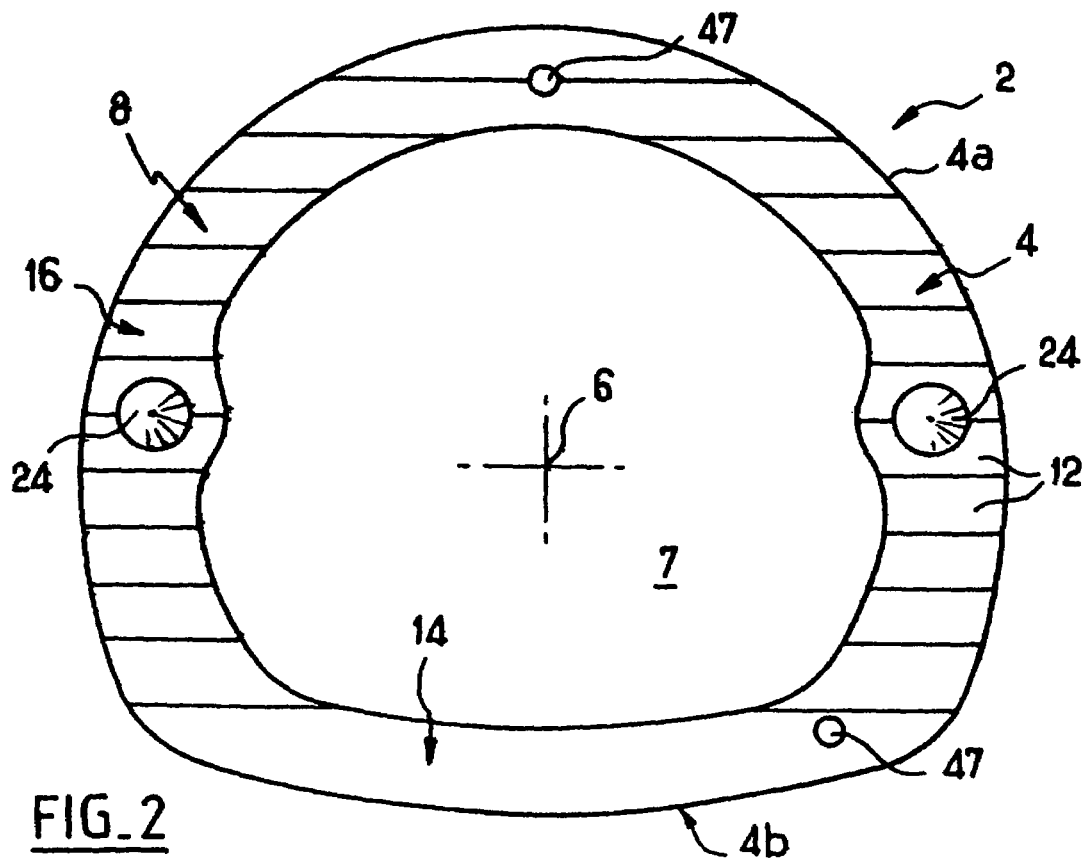
FIG_2

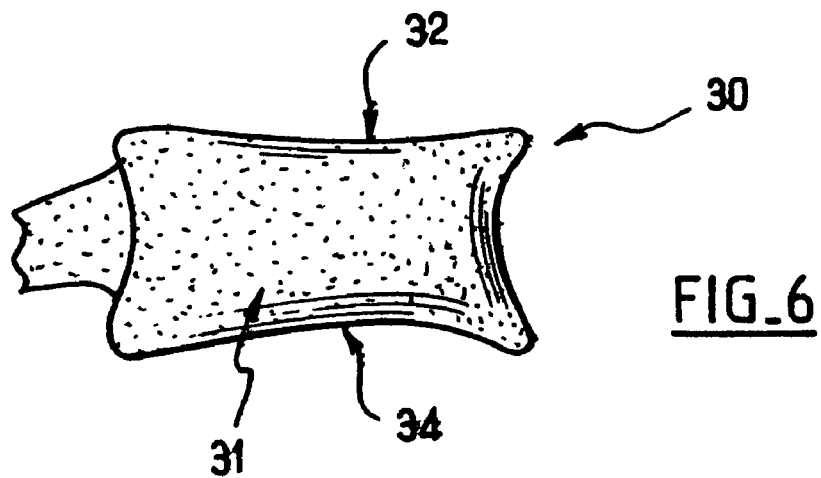
FIG_6
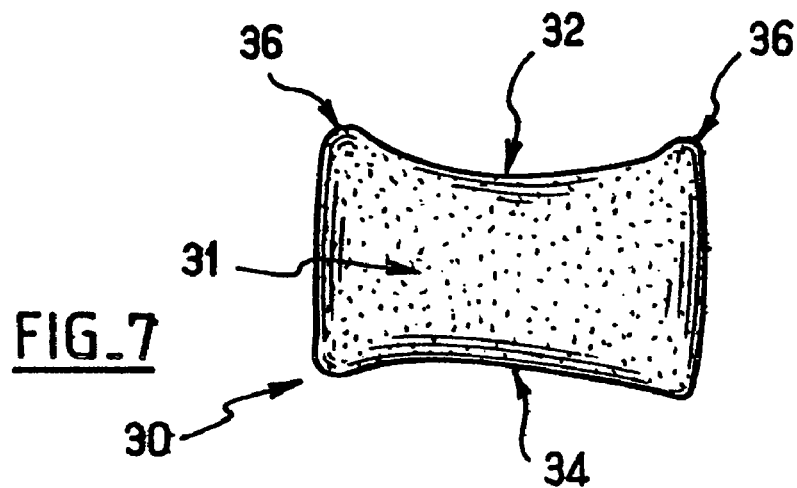
FIG_7
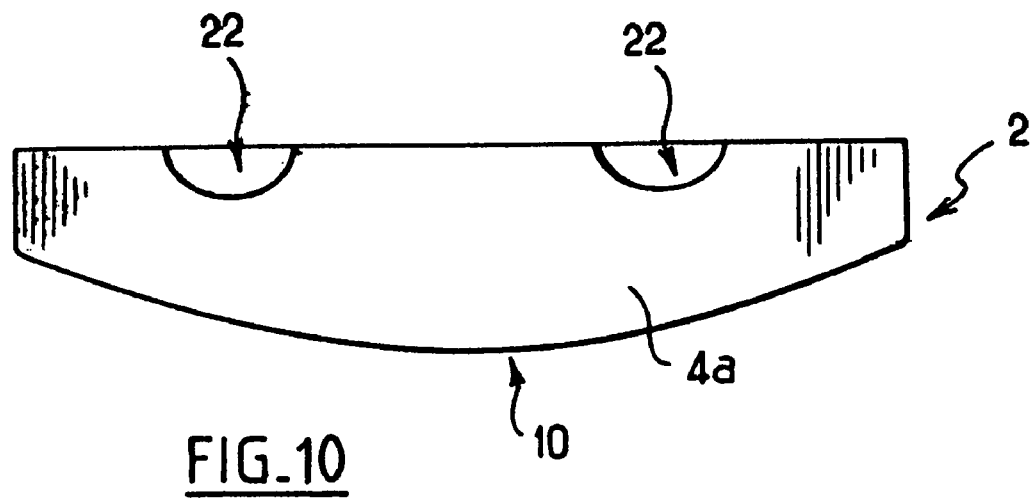
FIG_10

INTERVERTEBRAL IMPLANT WITH TOOTHED FACES

CROSS REFERENCE TO RELATED APPLICATIONS

The present application is a continuation-in-part of International Application PCT/FR00/02899, filed Oct. 18, 2000, which was published in French which claims priority from French Patent Application No. 99/12951 filed Oct. 18, 1999.

BACKGROUND OF THE INVENTION

The invention relates to intervertebral implants and more specifically to intervertebral implants that have mutually parallel elongate teeth on both main faces. Such teeth serve to anchor a prosthesis between vertebral bodies and adjacent to a disk space occupied by the implant.

An object of the present invention is to provide an implant that ensures even better anchoring between the prosthesis and the vertebral bodies.

In order to achieve this object, the present invention provides an intervertebral implant having two mutually opposite main faces, at least one of these faces having mutually parallel shaped teeth, in which the general shape of the profile of the toothed face, in at least one plane extending transversely to said face is curved.

Thus, the profile of the toothed face can be selected so as to be as complementary as possible to that of the vertebral plate with which the face of the implant is to come into contact. Whereas the prior art implants could require the face of the vertebral plate to be prepared by modifying its shape in order to improve contact with the implant, such preparation is usually pointless with the toothed face of the implant of the invention. This reduces the duration of the surgical operation required for installing the implant. The toothed and plate-shaped face makes it possible to achieve very high quality anchoring against the vertebral plate.

SUMMARY OF THE INVENTION

A preferred embodiment of the present invention includes an intervertebral implant having a pair of mutually opposite superior and inferior main faces and a side face. The superior face includes mutually parallel shaped teeth and at least one spike projecting from one of the main faces. Preferably the general shape of a profile of the superior tooth face is curved in at least one plane extending transversely to the face. The intervertebral implant may further include two segments having a generally rectangular shape and being inclined relative to each other. One of the two segments may be at least twice as long as the other segment. Furthermore, the tooth face may have a zone that does not have teeth disposed on one of the segments. The zone may be contiguous with an edge of the face.

The intervertebral implant may also include a central hole extending from one of the main faces to the other. An additional orifice may be disposed on the side wall of the implant and extend from an outer face of the side wall to the central hole.

The intervertebral implant according to one embodiment of the present invention may also include a side face having a first cylindrical portion extending more than 180° about a cylinder axis. The side face may also include a second cylindrical portion having a greater radius than the first cylindrical portion.

The teeth of the intervertebral implant may have a profile that slopes towards the same side of the implant and/or have a tapped orifice.

In one embodiment of the present invention, the intervertebral implant is preferably made of a bioresorbable material.

Any of the embodiments herein described may also be part of an intervertebral kit and coupled with a tool adapted for fitting the implant. The tool having fixing means for fixing the implant to the tool in a predetermined relative position and keying means adapted for insuring there is only one such position.

In a further additional embodiment, the intervertebral implant may include a pair of mutually opposite superior and inferior main faces and a side face. The side face having a first cylindrical portion extending more than 180° about a cylinder axis and a second cylindrical portion of greater radius than the first cylindrical portion. The superior face may also include mutually parallel shaped teeth having a curved profile and at least one plane extending transversely to the face.

BRIEF DESCRIPTION OF THE DRAWINGS

FIGS. 1 to 5 are respectively a perspective view, a plan view, a face view, a rear view, and a right-hand view of an implant constituting a preferred embodiment of the invention;

FIGS. 6 and 7 are section views of a cervical vertebra respectively in the sagittal and the frontal midplanes;

FIG. 10 is a fragmentary view analogous to FIG. 4 showing an additional embodiment of the present invention.

DETAILED DESCRIPTION

Figure 3:
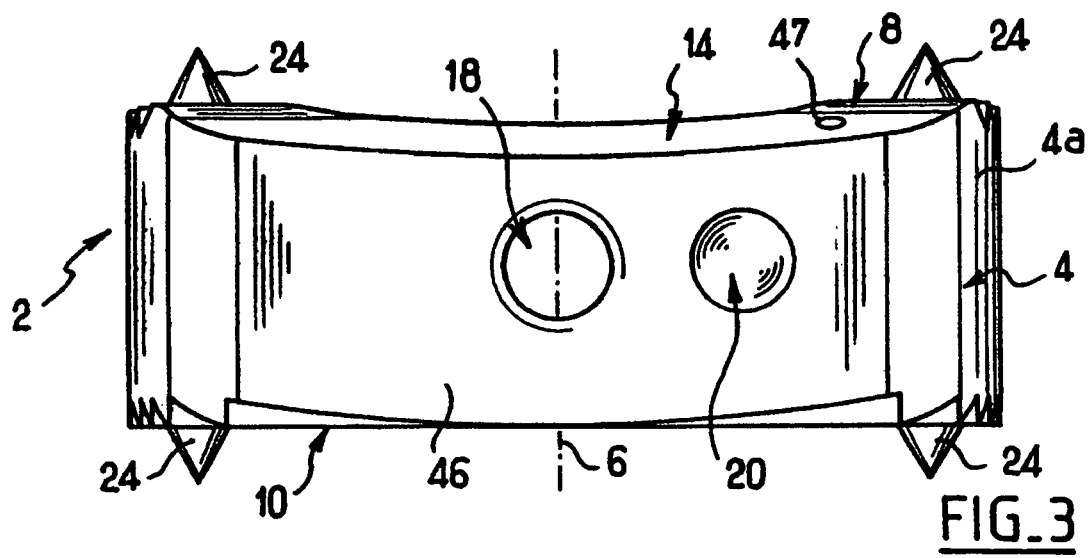
Figure 4:
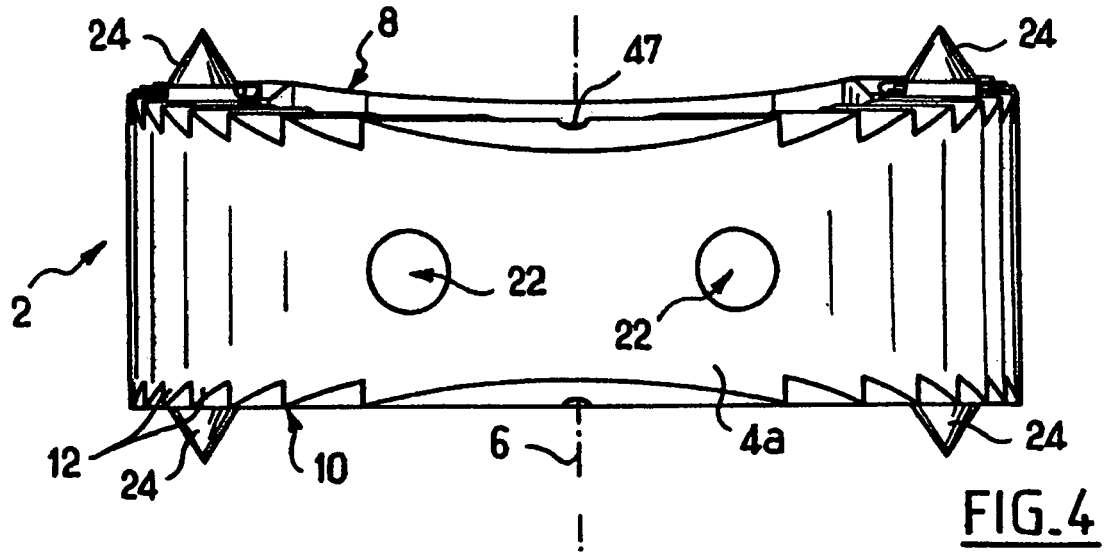
Figure 5:
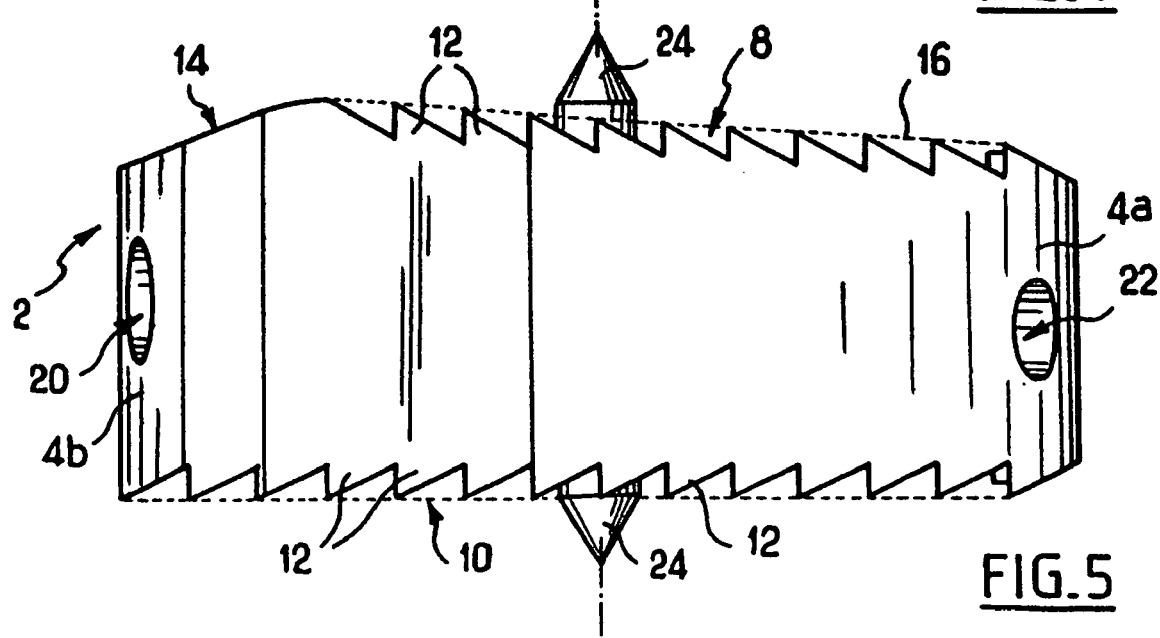

With reference to FIGS. 1 to 5, the implant 2 is constituted by a cage having a wall 4 that is generally annular about an axis 6.

In plan view, the wall has a first portion 4a that is horseshoe shaped. The portion 4a is cylindrical about the axis 6 and it extends over about 250° around the axis 6. The wall has a second portion 4b that is also cylindrical in shape, extending over about 20° about its own axis, which is not the axis 6 but is an axis parallel thereto. The radius of the second portion 4b is much greater than that of the first portion 4a. The ends of the first portion are joined to the ends of the second portion. In plan view, the cage is thus in the form of a ring that is somewhat flattened on a side 4b which in this case is the anterior or front side of the cage. This wall 4 defines a hole 7 in the center of the cage.

The cage has two main faces, a superior main face 8 and an inferior main face 10 that are opposite to each other and that extend generally in planes that are mutually parallel and perpendicular to the axis 6. The hole 7 extends between both faces 8 and 10.

The inferior face 10 in this case is precisely perpendicular to the axis 6. In a sagittal plane, i.e. parallel to the axis 6 and perpendicular to the front wall 4b, it presents a toothed profile forming mutually parallel elongate teeth 12 parallel to the front wall 4b. All of the teeth 12 are identical to one another and in particular they are all of the same height. All of the teeth slope forwards. Each of them has a front flank parallel to the axis 6 and a rear flank that slopes.

In the above-specified sagittal plane, the superior face 8 has a profile that is made up of two segments 14 and 16 of generally rectilinear shape that are inclined relative to each other so as to give the profile a shape that is convex.

The rear segment 16 is the longer of the two segments. In this plane, it extends over about 80% of the length of the cage. The segment has a profile that is toothed. All of the teeth 12 are identical to one another, and in particular they all have the same height. They slope forwards like the teeth of the inferior face 10. The segment 16 slopes slightly towards the rear of the cage. It is therefore slightly inclined relative to the inferior face 10.

The front segment 14 is inclined towards the front of the cage more steeply than the rear segment is inclined towards the rear. Its length is equal to about one-fourth the length of the rear segment 16. The front segment 14 is smooth. It corresponds to the portion of the superior face that extends over the front wall 4b. The two segments 14 and 16 give the top face 8 a profile that is similar to that of an airplane wing.

The cage has a threaded assembly and fixing orifice 18 extending in the sagittal midplane of the implant, in the front wall 4b, and permitting the outside face thereof into communication with the central hole 7. On one side of this orifice 18, e.g. on the right side thereof, the outer face of the front wall has a hemispherical cavity 20 which is used for keying purposes, as described below.

On the rearmost portion of the wall, the cage has two orifices 22 also putting the outer face into communication with the central hole 7. The two orifices 22 are disposed symmetrically about the sagittal midplane of the cage.

The cage has spikes 24, in this case four such spikes, i.e. two associated with each of the main faces 8 and 10. Each spike has a pointed end and it projects from the associated main face. The two spikes on each face are disposed symmetrically to each other about the sagittal midplane. In addition, they extend in the frontal midplane containing the axis 6. Each spike on one face extends in register with a spike on the other face.

The cage as described above is particularly adapted to occupying a cervical intervertebral space. FIGS. 6 and 7 show a vertebral body 31 of a cervical vertebra 30. In section on the sagittal midplane of FIG. 6, the superior plate 32 of the vertebra has a profile that is substantially horizontal and rectilinear while the inferior plate 34 has a profile that is concave, matching the profile of an airplane wing, and complementary to the convex profile of the superior face 8 of the cage. In section on a front midplane, as shown in FIG. 7, the inferior plate 34 has a profile that is substantially horizontal and rectilinear, while the superior plate 32 has a concave curved profile whose high points are the incus 36.

When the cage is inserted between two cervical vertebrae 31, the main faces 8 and 9 of the cage thus fit very closely to the shape of the plates 32 and 34 with which they come into contact.

Figure 8:
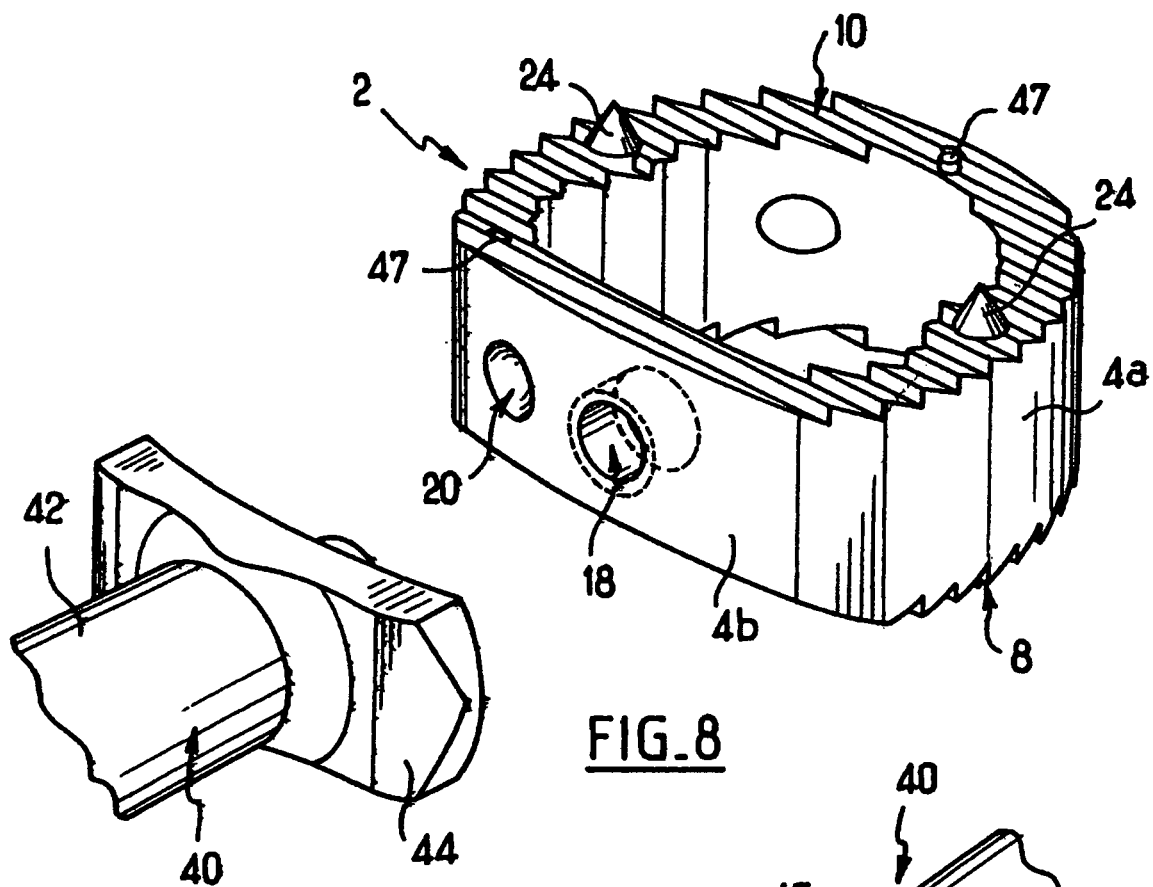
FIGS. 8 and 9 are perspective views of the FIG. 1 implant together with its fitting tool.
Figure 9:
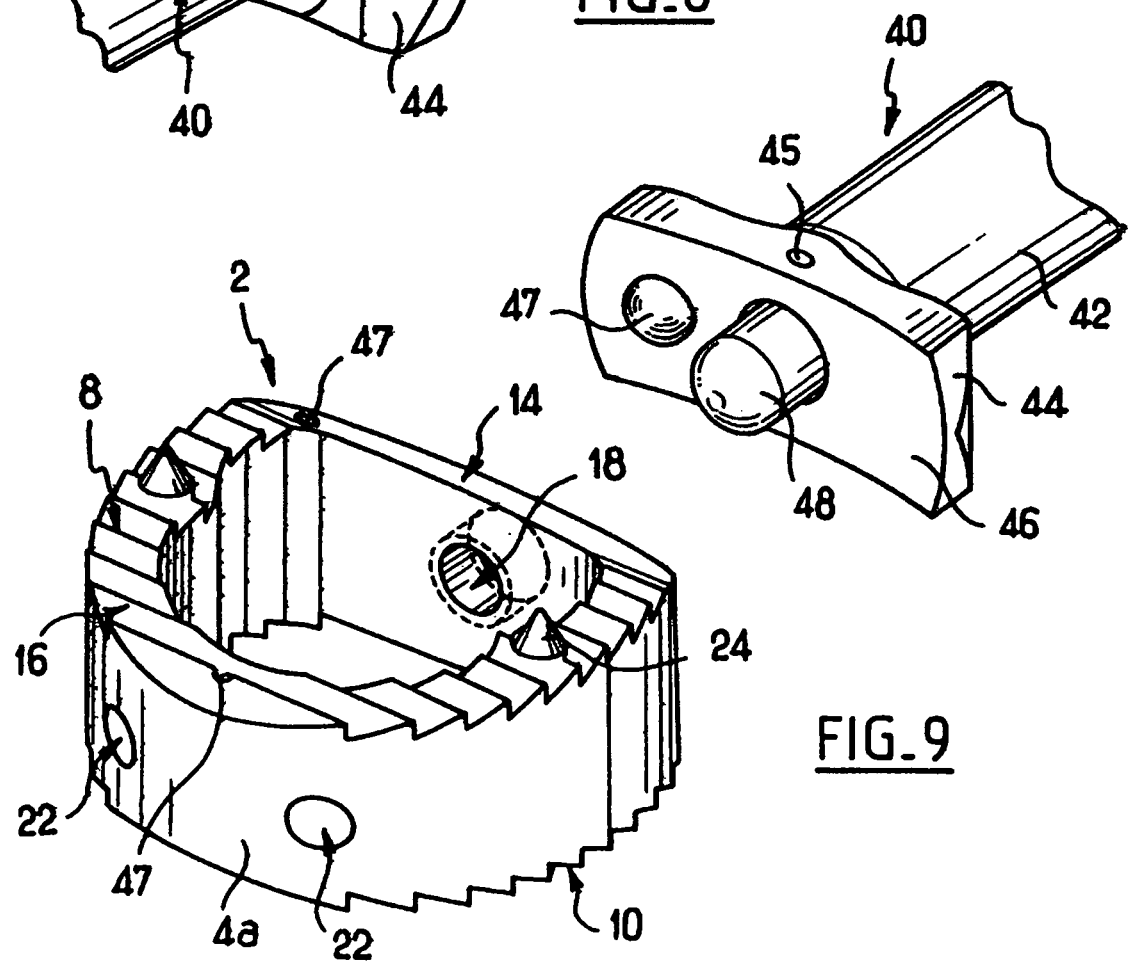

To put the cage into place, it is advantageous to use a fitting tool 40 such as the tool shown in FIGS. 8 and 9. This tool comprises a body 42 having a head 44 with a front face 46 of rectangular shape, whose shape and height are close to those of the front face of the cage 2. The tool has a threaded endpiece 48 emerging from the center of the face 46 of the head and movable relative thereto, being drivable from the other end of the tool. This endpiece is suitable for threaded engagement with the mounting orifice 18 of the cage. The front face 46 of the head has a spherical projection 47 suitable for penetrating in the front spherical cavity 20 of the cage when the endpiece 48 is connected to the orifice 18. The projection 47 and the cavity 20 together constitute keying means. Because of them, there is only one position in which the tool 40 can be fixed to the cage 2 with the outlines of the front face of the cage coinciding with those of the head 44 of the tool.

To put the cage into position between the vertebrae, the vertebrae are moved apart by appropriate means so as to increase the height of the disk gap between the vertebrae. The superior plate 32 of the inferior vertebra 10 is prepared so as to come close to the shape of the inferior face 10 of the cage. Prior to mounting, the hole 7 receives a bone graft or any other substance for enabling bone growth. With the cage mounted on the tool, the cage is put into place between the vertebrae from behind. The vertebrae are then allowed to move back towards each other. The vertebral plates 32 and 34 thus bear against the main faces 8 and 9 of the cage. The spikes 24 anchor themselves in the plates. After facilitating insertion of the cage, the orientation of the teeth 12 limits the ability of the cage to move forwards from its position. The cage does not require the inferior plate 34 of the superior vertebra to be prepared.

In an alternate embodiment as shown in FIG. 10, the inferior face of the cage, is still toothed (although that is not shown) and its shape in section parallel to the frontal plane is a convex circularly arcuate curve. Such a cage does not require the superior plate 32 of the inferior vertebra to be prepared and as a result there is no need to prepare any vertebral plate. Such a cage is therefore well adapted to cooperate with the anatomy of the intervertebral space.

The mounting orifice 18 can be used to fix the cage to an anchor system, e.g. an anterior prosthetic plate anchored elsewhere in the lateral faces of the vertebral bodies 31.

The orifices 18 and 22 facilitate vascularization of the graft received in the hole 7.

To further improve the keying, the head 44 of the tool can carry a mark 45 indicating the superior face 8 of the cage when the cage is properly fixed to the tool.

The cage can be made of a material that is transparent to X-rays, e.g. out of poly-ether-ether-ketone (PEEK). In which case, the cage can have one or more markers 47 included therein and serving, because they are opaque to X-rays, to identify the position and/or the presence of the implant when X-rays are taken during or after the operation. They could be made of titanium or of titanium alloy. In this case, there are two markers 47 and they are constituted by wires inserted in rectilinear ducts parallel to the axis 6 and formed in the wall of the cage. One of the ducts extends at the rear in the sagittal midplane, while the other extends at the left end of the front wall.

The spikes 24 can be inserted and fixed rigidly in the ducts formed in the cage. They too can be made of a material that is opaque to X-rays.

In another embodiment, the cage can be made of a material that is bioresorbable.

The invention claimed is:

1. An intervertebral implant comprising:
  a pair of mutually opposite superior and inferior main faces and a side face, wherein said superior main face includes mutually parallel shaped teeth and at least one spike, each of said teeth having a first side face and a second side face, said spike projecting from at least one of said first side face or said second side face of at least one tooth and upwardly beyond said teeth, said at least one spike intersecting at least one of said teeth, said spike differing in structure from said teeth, wherein the general shape of a profile of said superior main face in at least one plane extending transversely to said superior main face is curved and wherein said side face includes a first cylindrical portion extending more than 180 degrees about a first cylinder axis, and a second cylindrical portion of greater radius than said first cylindrical portion, the second cylindrical portion extending about a second cylinder axis, parallel to the first cylinder axis.

2. The intervertebral implant according to claim 1, wherein said profile of said superior main face has two segments of generally rectilinear shape that are inclined relative to each other.

3. The intervertebral implant according to claim 2, wherein one of said two segments is at least twice as long as the other segment.

4. The intervertebral implant according to claim 2, wherein said superior main face has a zone that is disposed on one of said segments said zone being devoid of teeth.

5. The intervertebral implant according to claim 1, wherein said superior main face has a zone that is without teeth and is contiguous with an edge of said superior main face.

6. The intervertebral implant according to claim 1, further comprising a central hole extending from one of said superior or inferior main faces to said other of said superior or inferior main faces.

7. The intervertebral implant according to claim 6, further comprising at least one orifice disposed on said side wall, said orifice extending from an outer face of said side wall to said central hole.

8. The intervertebral implant according to claim 1, wherein one of said first side face or said second side face of each of said teeth slopes towards said side face of the implant.

9. The intervertebral implant according to claim 1, comprising a tapped orifice.

10. The intervertebral implant according to claim 1, wherein the intervertebral implant is a cervical implant.

11. The intervertebral implant according to claim 1 wherein said inferior main face further includes at least one spike, said at least one spike of said superior main face and said at least one spike of said inferior main face being disposed symmetrically on a surface of said superior and inferior main faces about a sagittal midplane.

12. The intervertebral implant according to claim 11, further comprising two spikes on said inferior main face and two spikes on said superior main face.

13. An intervertebral kit comprising:
a pair of mutually opposite superior and inferior main faces and a side face, wherein said superior main face includes mutually parallel shaped teeth and at least one spike, each of said teeth having a first side face and a second side face, said spike projecting from at least one of said first side face or said second side face of at least one tooth and upwardly beyond said teeth, said at least one spike intersecting at least one of said teeth, wherein the general shape of a profile of said superior main face in at least one plane extending transversely to said superior main face is curved and wherein said side face includes a first cylindrical portion extending more than 180 degrees about a first cylinder axis, and a second cylindrical portion of greater radius than said first cylindrical portion, the second cylindrical portion extending about a second cylinder axis, parallel to the first cylinder axis; and a tool adapted for fitting the intervertebral implant and having fixing means for fixing the implant to said tool in a predetermined relative position and keying means adapted for ensuring there is only one such position.

14. An intervertebral implant comprising:
a pair of mutually opposite superior and inferior main faces and a side face, wherein said side face includes a first cylindrical portion extending more than 180 degrees about a first cylinder axis and a second cylindrical portion of greater radius than said first cylindrical portion, the second cylindrical portion extending about a second cylinder axis, parallel to the first cylinder axis, wherein said superior main face includes mutually parallel shaped teeth, and at least one spike, each of said teeth having a first sidewall and a second sidewall, said at least one spike intersecting at least one of said teeth and positioned between said first sidewall and said second sidewall, wherein said superior main face has a curved profile in at least one plane extending transversely to said superior main face.

15. The intervertebral implant according to claim 14, wherein said profile of said superior main face presents two segments of generally rectilinear shape that are inclined relative to each other.

16. The intervertebral implant according to claim 15, wherein one of said two segments is at least twice as long as the other segment.

17. The intervertebral implant according to claim 15, wherein said superior main face has a zone that forms one of said segments and does not have teeth.

18. The intervertebral implant according to claim 17, further comprising at least one orifice disposed on said side wall, said orifice extending from an outer face of said side wall to said central hole.

19. The intervertebral implant according to claim 14, wherein said superior main face has a zone that is without teeth and is contiguous with an edge of said superior main face.

20. The intervertebral implant according to claim 14, further comprising a central hole extending from one of said superior or inferior main faces to said other of said superior or inferior main faces.

21. The intervertebral implant according to claim 14, wherein said side face includes a front wall and a rear wall and wherein one of said first sidewall or second sidewall of each of said teeth slopes toward said front wall or said rear wall.

22. The intervertebral implant according to claim 14, comprising a tapped orifice.

23. The intervertebral implant according to claim 14, wherein the intervertebral implant is a cervical implant.

* * * * *